United States Patent [19]

Ishikawa et al.

[11] Patent Number: 4,552,694

[45] Date of Patent: Nov. 12, 1985

[54] FLUORINATED BENZODIAZEPINS

[75] Inventors: Nobuo Ishikawa, Yokohama; Akio Takaoka, Kawasaki, both of Japan

[73] Assignee: Daikin Industries Ltd., Osaka, Japan

[21] Appl. No.: 635,681

[22] Filed: Jul. 30, 1984

[30] Foreign Application Priority Data

Jul. 30, 1983 [JP] Japan .................. 58-140118

[51] Int. Cl.[4] .......................................... C07D 243/12
[52] U.S. Cl. ...................... 260/239 BD; 260/239.3 B; 514/221
[58] Field of Search ................... 260/239 BD, 239.3 B

[56] References Cited

U.S. PATENT DOCUMENTS 2,899,359  8/1959  Fancher et al. ............... 260/239 BD
3,021,325  2/1962  Fancher et al. ............... 260/239 BD Primary Examiner—Robert T. Bond
Attorney, Agent, or Firm—Armstrong, Nikaido, Marmelstein & Kubovcik

[57] ABSTRACT

New fluorinated benzodiazepins are described. They are expressed by the following general formula:

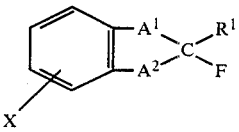

wherein $A^1$ and $A^2$ are the same or different groups, each expressed by one of the following general formulas

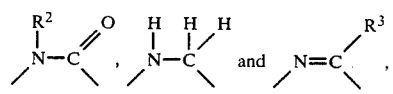

$R^2$ being a hydrogen atom, aliphatic hydrocarbon group, fluorine-substituted aliphatic hydrocarbon group, aminoalkyl, N,N-dialkylaminoalkyl, or alkylsulfonylalkyl group and $R^3$ a hydrogen atom, aliphatic or aromatic hydrocarbon group, halogen-substituted aliphatic or aromatic hydrocarbon group, while $R^1$ is a hydrogen atom, aliphatic or aromatic hydrocarbon group, fluorine-substituted aliphatic or aromatic hydrocarbon group and X is a hydrogen atom, aliphatic hydrocarbon group, fluorine-substituted aliphatic hydrocarbon group, halogen atom, nitro group or the like.

4 Claims, No Drawings

FLUORINATED BENZODIAZEPINS

BACKGROUND OF THE INVENTION

1. Field of the Invention

This invention relates to new fluorinated benzodiazepins.

2. Description of the Prior Art

Some mono-fluorinated compounds are known to exhibit useful physiological activities.

OBJECTS AND SUMMARY OF THE INVENTION

It is an object of the present invention to provide new and useful fluorinated benzodiazepins. This object is accomplished according to the invention by fluorinated benzodiazepins of the formula.

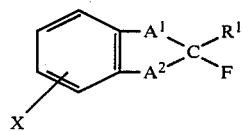

wherein $A^1$ and $A^2$ are the same or different groups, each expressed by one of the following general formulas

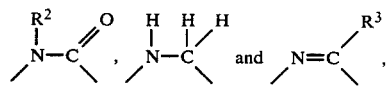

$R^2$ being a hydrogen atom, aliphatic hydrocarbon group, fluorine-substituted aliphatic hydrocarbon group, aminoalkyl, N,N-dialkylaminoalkyl, or alkylsulfonylalkyl group and $R^3$ a hydrogen atom, aliphatic or aromatic hydrocarbon group, halogen-substituted aliphatic or aromatic hydrocarbon group, while $R^1$ is a hydrogen atom, aliphatic or aromatic hydrocarbon group, fluorine-substituted aliphatic or aromatic hydrocarbon group and X is a hydrogen atom, aliphatic hydrocarbon group, fluorine-substituted aliphatic hydrocarbon group, halogen atom, nitro group or the like.

The above fluorinated benzodiazepins are useful as physiologically active substances, such as insecticide and disinfectant, or intermediates to synthesize building blocks of these substances.

Other objects and advantages of the invention will become apparent from the following description of embodiments.

DESCRIPTION OF THE PREFERRED EMBODIMENTS

In the fluorinated benzodiazepins of the invention, the groups $A^1$ and $A^2$ respectively contain a nitrogen atom necessary to form a diazepin ring. Basically, they are provided in one of the following three forms

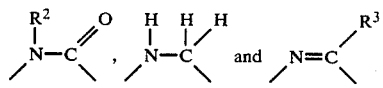

Therefore, there is possible to be a variety of the fluorinated benzodiazepins. Among these compounds, preferred is compound of the formula

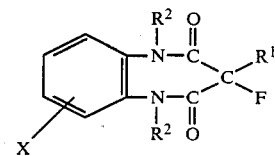

or

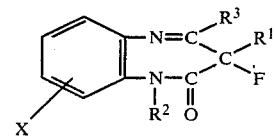

Among the group $R^2$ is preferred a hydrogen atom, alkyl, fluoralkyl, alkenyl, aminoalkyl, N,N-dialkylaminoalkyl, or alkylsulfonylalkyl group, containing up to ten carbon atoms. Examples of such $R^2$ are hydrogen atom, methyl, ethyl, propyl, butyl, c-propylmethyl, trifluoroethyl, N,N-diethylaminoethyl, and methylsulfonylethyl groups.

Among the group $R^3$ is preferred a hydrogen atom, alkyl, fluoroalkyl, phenyl, fluorophenyl or chlorophenyl group containing up to ten carbon atoms. The $R^3$ may thus be selected among the alkyl, fluoroalkyl, alkenyl and fluoroalkenyl groups cited above for the group $R^2$. For example, it may represent a trifluoromethyl group. Further examples of the $R^3$ are phenyl and other aryl groups which may have floro, chloro and/or fluoroalkyl substituent or substituents. For example, it may be

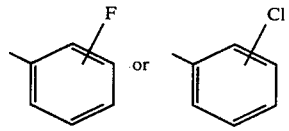

The group $R^1$ is preferably a hydrogen atom, alkyl, fluroalkyl, alkenyl or fluoroalkenyl group having up to five carbon atoms. The $R^1$ may thus be one of the alkyl, fluroalkyl, alkenyl and fluoroalkenyl groups cited above for the $R^2$ and $R^3$ as far as the number of carbon atoms are limited to five. For example, methyl, ethyl, propyl and butyl groups are preferable. Further, the group $R^1$ may be a phenyl, fluorophenyl or other aryl group, or even an aralkyl group.

It is noted that in the above fluorinated groups, for example, in the "fluoralkyl group" the number of substituent fluorine atoms and their positions may be variously changed.

Further, in the above general formula representing the fluorinated benzodiazepins of the invention, the substituent X on the benzene ring is preferably one of the alkyl and alkenyl groups having up to five carbon atoms as cited above for $R^1$, for example, methyl group, or halogen atom, such as chlorine or fluorine atom, nitro group or the like.

At least having a fluorine atom at the 3-position of their heterocyclic ring, the fluorinated benzodiazepins of the invention are physiologically active and expected to have other properties that are characteristic of the fluorinated compound.

The fluorinated benzodiazepins of the invention can be prepared by a process defined by a series of reaction formulas as given next. First, hexafluoropropene ($CF_3CF=CF_2$) is reacted in a solution of sodium ethoxide in ethanol to form an adduct 1, which is then hydrolized to an ester 2 by sulfuric acid or the like. This ester is again reacted in a solution of sodium ethoxide in ethanol for conversion of its $CF_3$ group to an ester group to produce fluoromalonic ester 3. The ester 3 is alkylated by the ordinary method to synthesize an alkylated product 4. The α-fluoro-β-diesters 3 and 4 thus prepared can be used for the synthesis of fluorinated benzodiazepins as mentioned later.

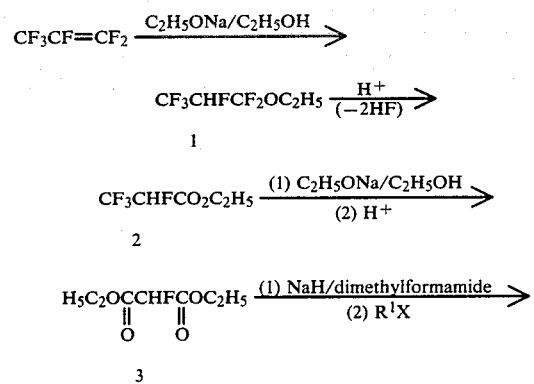

($R^1$ = group as defined above, for example, $CH_3$—, $C_2H_5$—, $C_4H_9$—, etc.)

Meanwhile, according to the following series of reaction formulas, trifluoroethene ($CHF=CF_2$) is reacted with acetyl chloride in presence of $AlCl_3$ to form an adduct 5, which is then alcoholized to give α-fluro-β-ketoester 6 that can be used for synthesis of fluorinated benzodiazepins of the invention.

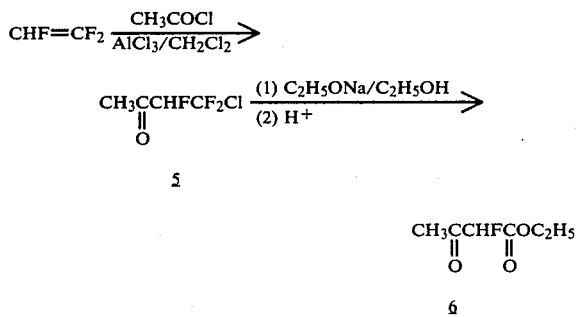

Further, according to the following series of reaction formulas, an adduct 7 and substitution product 8 are produced by the reaction of hexafluoropropene and diethylammonium and they are hydrolized to an amide 9, which is then reacted with $R^3MgBr$ wherein $R^3$ is one of the preferable groups as cited above for $R^3$ to produce a ketone 10 that can be alcoholized by the ordinary method to α-fluorobenzoylacetic ester 11.

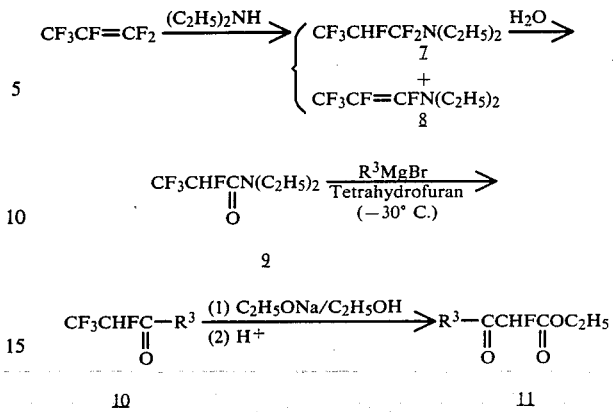

The above products 3, 4, 6 and 11 can be used to synthesize fluorinated benzodiazepins of the invention by methods as described below.

Synthesis of 1H-3-fluoro-1,5-benzodiazepin-2,4(3H,5H)-dione 12

O-phenylenediamine and fluoromalonic ester 3 are dissolved in a solution of sodium ethoxide in ethanol and the solution is refulxed for 1 to 10 hours for a reaction to produce a benzodiazepin 12 in high yield according to the following reaction formula. The alkylated product 4 of fluoromalonic ester 3 is likewise reacted to give the corresponding benzodiazepin 12 in high yield.

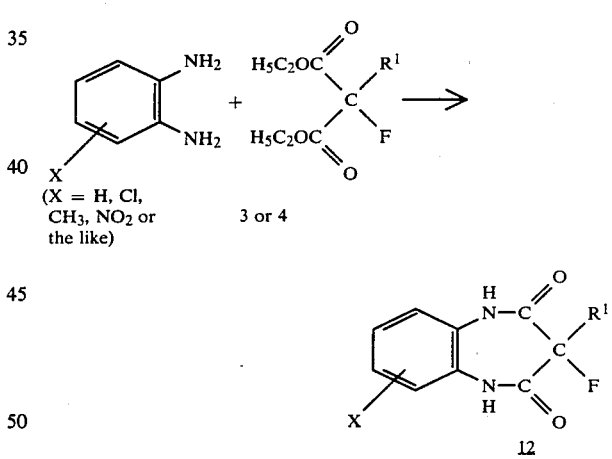

Solvents applicable for this reaction can be aprotic polar solvent, for example, dimethylformamide, dimethylsulfoxide and sulfolane wherein bases such as Na, K, NaH are used. Reaction temperature can be 50° to 150° C. and reaction pressure can be atmospheric or reduced pressure.

When the $R^1$ was variously changed in the above reaction, the target compound 12 was produced in high yield as the corresponding products as listed in the following table:

| Product 12 | | Yield | M.P. | IR (cm$^{-1}$) | | $^{19}$FNMR |
|---|---|---|---|---|---|---|
| $R^1$ | X | (%) | (°C.) | (CO) | (NH) | ppm ($^1$H–F) |
| H | H | 61 | >300 | 1680 | 3200 | 132.1d(J39.5) |
| H | $CH_3$— | 72 | >300 | 1670 | 3260 | 130.0d(J39.5) |

-continued

| Product 12 | | Yield | M.P. | IR (cm$^{-1}$) | | $^{19}$FNMR |
|---|---|---|---|---|---|---|
| R$^1$ | X | (%) | (°C.) | (CO) | (NH) | ppm ($^J$H-F) |
| H | Cl | 44 | >300 | 1690 | 3340 | 129.5d(J39.5) |
| H | NO$_2$ | 52 | 262 | 1690 | 3350 | 119.5d(J39.5) |
| CH$_3$— | H | 59 | 245 | 1680 | 3200 | 78.0q(J20.7) |
| C$_2$H$_5$— | H | 62 | 283 | 1660 | 3170 | 87.5t(J19.8) |
| C$_4$H$_9$— | H | 48 | 204 | 1690 | 3200 | 85.5t(J18.8) |

Further, when reacted with R$^2$Y, wherein R$^2$ is one of the groups as mentioned above for such and Y is a halogen atom, for example, I, the benzodiazepin 12 is readily substituted with a group R$^2$ according to the following formula. For example, when reacted with CH$_3$I, it is methylated. A protected and stabilized benzodiazepin derivative 13 can thus be prepared.

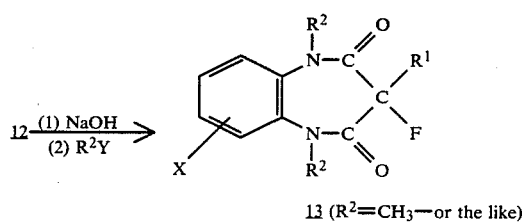

13 (R$^2$=CH$_3$— or the like)

Solvents applicable for this reaction can be alcohol such as ethanol as well as aprotic polar solvent already described. Reaction temperature can be 20° to 100° C. and reaction pressure can be atmospheric or reduced pressure. The same benzodiazepin 12 can also be converted to other benzodiazepin 14 or 15 according to the following reaction formulas:

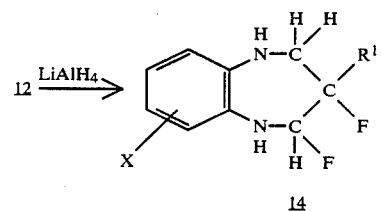

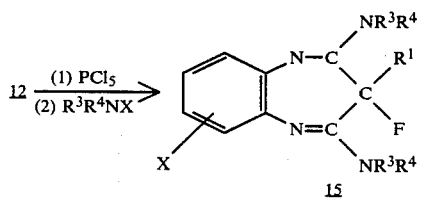

Synthesis of 1H-3-fluoro-4-phenyl-1,5-benzodiazepin-2-one 16

O-phenylenediamine and α-fluorobenzoylacetic ester 11 are put in a mixed solvent of CH$_3$COOH/C$_2$H$_5$OH and refluxed to form a benzodiazepin 16 in high yield (for example, 43 to 65%) according to the following reaction formula.

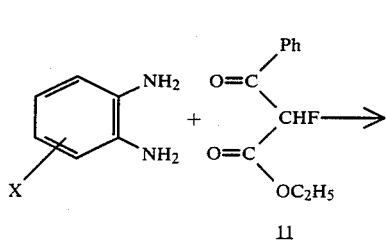

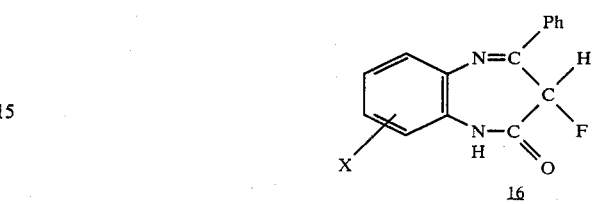

It is noted that the phenyl group Ph on the heterocyclic ring of the product 16 may be a different R$^3$ as mentioned above. For example, a benzodiazepin 17 wherein R$^3$=CH$_3$—, can be prepared by the following reaction:

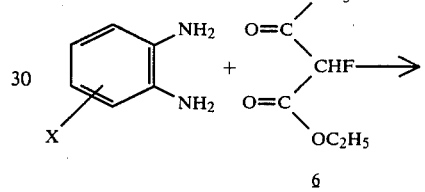

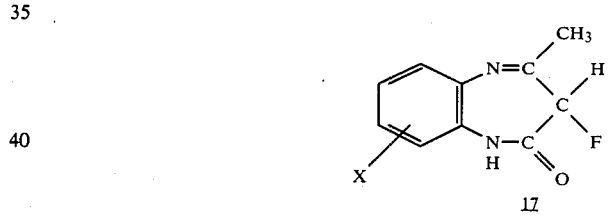

Solvent usable for the reactions to produce 16 and 17 can be aprotic polar solvent already described, reaction temperatures can be 50° to 150° C. and reaction pressure can be atmospheric.

On the other hand, β-perfluoroalkyl-β-ketoesters 11' and 11" can be prepared by the crossed Claisen condensation according to the following reaction formulas, which may also be used for synthesis of fluorinated benzodiazepins of the present invention.

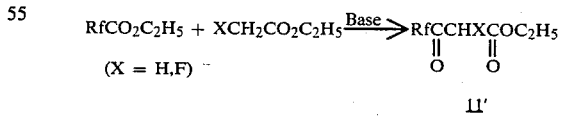

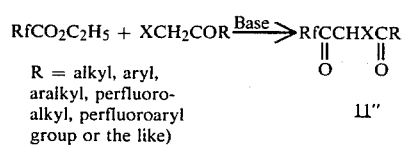

R = alkyl, aryl, aralkyl, perfluoroalkyl, perfluoroaryl group or the like

The present invention will be more clearly understood with reference to the following examples.

EXAMPLE 1

O-phenylenediamine (1.1 g, 10 mmol) and ethyl fluoromalonate (1.8 g, 10 mmol) were added to a solution of sodium ethoxide (0.68 g, 10 mmol) in ethanol (10 ml). The mixture was refluxed 5 hours and left to stand overnight at room temperature. The solution was then acidified by hydrochloric acid and precipitates were separated by filtration. Recrystallization from acetic acid gave 1.2 g of a white crystalline product of a melting point above 300° C. (61%).

EXAMPLE 2

P-chloro-o-phenylenediamine (1.5 g, 10 mmol) and ethyl fluoromalonate (1.8 g, 10 mmol) were added to a solution of sodium ethoxide (0.68 g, 10 mmol) in ethanol (10 ml). The same process as applied to Example 1 gave 1.0 g of a crystalline product of a melting point above 300° C. (44%).

EXAMPLE 3

P-nitro-o-phenylenediamine (1.6 g, 10 mmol) and ethyl fluoromalonate (1.8 g, 10 mmol) were added to a solution of sodium ethoxide (0.68 g, 10 mmol) in ethanol (10 ml). The same process as applied to Example 1 was repeated except that methanol was used for recrystallization. There was produced 1.3 g of crystalline product of a melting point 262° (52%).

EXAMPLE 4

P-methyl-o-phenylenediamine (1.3 g, 10 mmol) and ethyl fluoromalonate (1.8 g, 10 mmol) were added to a solution of sodium ethoxide (0.68 g, 10 mmol) in ethanol (10 ml). The same process as applied to Example 1 was repeated except that methanol was used for recrystallization. There was produced 1.5 g of a crystalline product of a melting point above 300° C. (72%).

EXAMPLE 5

O-phenylenediamine (1.1 g, 10 mmol) and ethyl 2-fluoro-2-methylmalonate (1.95 g, 10 mmol) were added to a solution of sodium ethoxide (0.68 g, 10 mmol) in ethanol (10 ml). The mixture was refluxed 5 hours and left to stand overnight at room temperature. The solution was then acidified by hydrochloric acid and precipitates were separated by filtration. Recrystallization from methanol gave 1.25 g of a crystalline product of a melting point above 245° C. (59%).

EXAMPLE 6

In Example 5, ethyl 2-fluoro-2-ethylmalonate (2.15 g, 10 mmol) was used in place of ethyl 2-fluoro-2-methylmalonate. The same procedure as Example 5 were performed. Recrystallization from ethanol gave a product of melting point 283° C. in a yield of 62%.

EXAMPLE 7

O-phenylenediamine (1.1 g, 10 mmol) and ethyl 2-fluoro-2-butylmalonate (2.35 g, 10 mmol) were added to a solution of sodium ethoxide (0.68 g, 10 mmol) in ethanol (10 ml). The same process as applied to Example 5 was repeated except that water was used for recrystallization. There was given 1.25 g of a crystalline product of a melting point 204° C. (48%)

EXAMPLE 8

Methyl iodide (2.9 g, 20 mmol) was added dropwise in half an hour to a solution of 1H-3-fluoro-1,5-benzodiazepin-2,4(3H,5H)-dione (1.95 g, 10 mmol) and sodium ethoxide (0.68 g, 10 mmol) in ethanol (20 ml). The mixture was refluxed 3 hours. After cooling, it was acidified and precipitates were separated by filtration. Recrystallization from methanol gave 1.2 g of a needle-like crystalline product of a melting point above 300° C. (55%). This product showed the following analytical data.

Anal. Found: C,59.21; H,4.87; N,12.74%. Calcd. for $C_9H_{11}N_2O_2F$. C,59.45; H,4.98; N,12.60%.

IRνmax. (KBr) 1722,1700,1600 cm$^{-1}$. (CO,C=N, stretching).

$^{19}F$ NMR δ(neat)+126.o,d,J=45.16 Hz,1F,CHF.

$^1H$ MNR δ(DMSO-d$_6$) 3.3,s,6H,2CH$_3$; 5.33, d,j=48.5 Hz, 1H, CHF; 7.19,s,4H,Ar—H.

EXAMPLE 9

Ethyl 1,1,1-trifluoro-3-fluoro-acetylacetate (1.85 g, 10 mmol) and o-phenylenediamine (1.1 g, 10 mmol) were added in a mixed solvent (25 ml of ethyl alcohol plus 10 ml of acetic acid). After refluxing 5 hours, solvent was evaporated. Recrystallization of residues from ethanol gave 1.85 g of a crystalline product of a melting point 165° C. (80% ).

EXAMPLE 10

Using ethyl 1,1,1-trifluoro-3-fluoro-acetylacetate (1.85 g, 10 mmol) and p-methyl-o-phenylenediamine (2.45 g, 10 mmol), the process of Example 8 was repeated. There was thus produced 2.3 g of a crystalline product of a boiling point 198° C. (95%).

EXAMPLE 11

Using ethyl 1,1,1-trifluoro-3-fluoro-acetylacetate (1.85 g, 10 mmol) and p-chloro-o-phenylenediamine (2.65 g, 10 mmol), the process of Example 8 was repeated. There was produced 2.1 g of a crystalline product of a melting point 237° C. (75%).

EXAMPLE 12

O-phenylenediamine (1.08 g, 10 mmol) and trifluorobenzoylacetone (2.0 g, 10 mmol) were suspended in acetic acid and heated 3 hours at 80° C. After the mixture cooled down, it was poured into iced water and precipitates thereby formed were separated by filtration. Recrystallization from chloroform gave 1.9 g of a crystalline product of a melting point of 208° C. (65%).

Anal. Found: Calcd. for $C_{16}H_{11}N_2F_3$. C,66.66; H,3.84; N,9.71%.

IR ν max. (KBr) 1598 cm$^{-1}$. (C=N, stretching).

$^{19}F$δNMR (neat) −13.2s,3F,CF$_3$.

$^1H$δNMR (DMSO-d$_6$/CCl$_4$) 3.4,s,2H,CH$_2$; 7.33–8.0,m,9H,Ar—H. MS (m/e) 288 (M$^+$)

EXAMPLES 13 to 15

Refluxing of ethyl α-fluorobenzoylacetate (2.25 g, 10 mmol) with o-phenylenediamine (10 mmol) in the mixture of acetic acid and ethanol (25%) for 5 h gave 3-fluoro-1,5-benzodiazepin-2-one derivatives in good yields as follows.

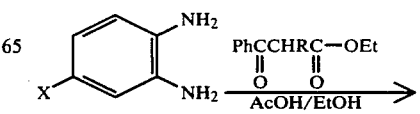

-continued

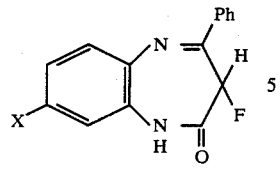

wherein X=H, 4-Me, 4-Cl or NO₂. It is clear that the first step of this reaction is condensation of carbonyl ketone and amine by losing water and second step is cyclization of their ester with another amine by losing ethanol. When used p-CH₃ or p-Cl o-phenylenediamine, these were condensed with α-fluorobenzoylacetate, Products in the above Examples as well as other products that were produced according to the invention are listed in Tables 1, 2, and 3 together with their physical and analytical data.

It will be evident that various modifications can be made to the described embodiments without departing from the scope of the present invention.

What is claimed is:

1. A fluorinated benzodiazepin of the formula

TABLE 2

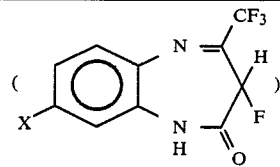

| Example No. | Product X | M.P. (°C.) | Yield (%) | IR (cm⁻¹) [C=N] | [CO] | [NH] |
|---|---|---|---|---|---|---|
| 9 | H | 165 | 80 | 1600 | 1680 | 3210 |
| 10 | CH₃ | 198 | 95 | 1605 | 1685 | 3200 |
| 11 | Cl | 237 | 75 | 1600 | 1690 | 3200 |

TABLE 3

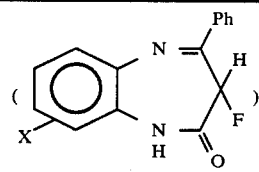

| Example No. | Product X | M.P. (°C.) | Yield (%) | IR (cm⁻¹) [C=N] | [CO] | [NH] | NMR ¹⁹F δ ppm(ᴶHF) | ¹H δ ppm | MS (m/e) [M⁺] |
|---|---|---|---|---|---|---|---|---|---|
| 13 | H | 178 | 53 | 1605 | 1685 | 3400 | 124 d(41.4) | 5.45 d(CHF), 7.30~8.20 m(Ar—H) 11.17 s(NH) | 254 |
| 14 | CH₃ | 188 | 61 | 1620 | 1690 | 3430 | 123 d(43.2) | 2.40 s(CH₃), 5.51d(CHF) 7.00~8.05 m(Ar—H), 10.93 s(NH) | 268 |
| 15 | Cl | 252 | 45 | 1600 | 1680 | 3420 | 122 d(41.8) | 5.56 d(CHF), 7.17~8.28 m(Ar—H) 11.23 s(NH) | |

TABLE 1

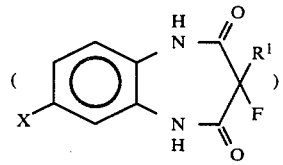

| Example No. | Product R¹ | X | M.P. (°C.) | Yield (%) | IR (cm⁻¹) [CO] | [NH] | NMR ¹⁹F δ ppm(ᴶHF) | ¹H δ ppm | Elementary analysis theor. values in parentheses C (%) | H (%) | N (%) |
|---|---|---|---|---|---|---|---|---|---|---|---|
| 1 | H | H | >300 | 61 | 1680 | 3200 | 132.1 d(J 39.5) | 5.45 d(CHF), 7.16 s(Ar—H) 10.76 s(NH × 2) | 56.03 (55.67) | 3.65 (3.63) | 14.54 (14.43) |
| 4 | H | Me | >300 | 72 | 1670 | 3260 | 130.0 d(J 39.5) | 2.20 s(CH₃), 5.45 d(CHF) 7.07 s(Ar—H), 10.50 s(NH × 2) | 57.60 (57.69) | 4.59 (4.36) | 13.32 (13.43) |
| 2 | H | Cl | >300 | 44 | 1690 | 3340 | 129.5 d(J 39.5) | 5.44 d(CHF), 7.11 s(Ar—H) 10.30 s(NH × 2) | 47.03 (47.20) | 2.48 (2.64) | 11.99 (12.25) |
| 3 | H | NO₂ | 262 | 52 | 1690 | 3350 | 119.5 d(J 39.5) | 5.70 d(CHF), 7.40~8.10 m(Ar—H) 10.45 s(NH × 2) | 44.54 (45.19) | 2.53 (2.52) | 17.29 (17.56) |
| 5 | Me | H | 245 | 59 | 1680 | 3200 | 78.0 q(J 20.7) | 1.33 d(CH₃), 7.16 s(Ar—H) 10.69 s(NH × 2) | 57.67 (57.69) | 4.57 (4.36) | 13.31 (13.45) |
| 6 | Et | H | 283 | 62 | 1660 | 3170 | 87.5 t(J 19.8) | 0.87 t(CH₃), 1.80 dq(CH₂) 7.23 s(Ar—H), 10.98 s(NH × 2) | 59.34 (59.46) | 4.91 (4.99) | 12.56 (12.61) |
| 7 | Bu | H | 204 | 48 | 1690 | 3200 | 85.5 t(J 18.8) | 0.66 t(CH₃), 1.00~1.30 m(C₂H₄) 1.60 dt(CFCH₂) 7.17 s(Ar—H), 10.90 s(NH × 2) | 62.15 (62.38) | 6.06 (6.04) | 11.13 (11.19) |

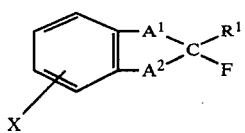

wherein $A^1$ and $A^2$ are the same or different groups, each expressed by one of the following formulas

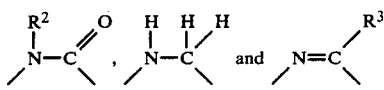

$R^2$ being a hydrogen atom or a group having up to 10 carbon atoms selected from the group consisting of alkyl, alkenyl, fluorine-substituted alkyl, fluorine-substituted alkenyl, aminoalkyl, N,N-dialkylaminoalkyl and alkylsulfonylalkyl, and $R^3$ being a hydrogen atom or a group having up to 10 carbon atoms selected from the group consisting of alkyl, alkenyl, phenyl, halogen-substituted alkyl, halogen-substituted alkenyl and halogen-substituted phenyl, while $R^1$ is a hydrogen atom, phenyl, fluorine-substituted phenyl or a group having up to 5 carbon atoms selected from the group consisting of alkyl, alkenyl fluorine-substituted alkyl and fluorine-substituted alkenyl, and X is a hydrogen atom, halogen atom, nitro group or a group having up to 5 carbon atoms selected from the group consisting fo alkyl, alkenyl or fluorine-substituted alkyl and fluorine-substituted alkenyl.

2. A fluorinated benzodiazepin as claimed in claim 1, wherein said formula thereof is either

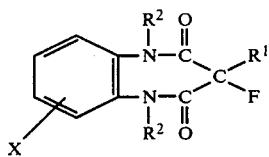

or

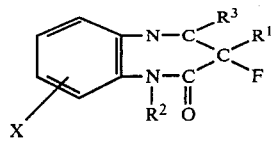

3. A fluorinated benzodiazepin as claimed in claim 1, wherein said X is a hydrogen atom, alkyl group having up to five carbon atoms, chlorine or fluorine atom, or nitro group; said $R^1$ is a hydrogen atom or a group having up to 5 carbon atoms selected from the group consisting of alkyl, fluoroalkyl, alkenyl and fluoroalkenyl; said $R^2$ is a hydrogen atom or a group having up to 10 carbon atoms selected from the group consisting of alkyl, fluoroalkyl, aminoalkyl, N,N-dialkylaminoalkyl and alkylsulfonylalkyl; and said $R^3$ is a hydrogen atom, alkyl or fluoroalkyl group having up to 10 carbon atoms, phenyl, fluorophenyl or chlorophenyl group.

4. A fluorinated benzodiazepin of the formula

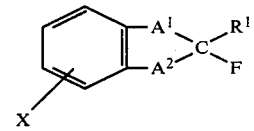

wherein $A^1$ and $A^2$ are the same or different groups, each expressed by one of the following formulas

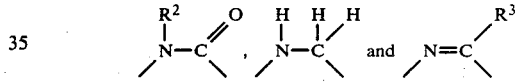

wherein X is a hydrogen atom, methyl group, chlorine atom, or nitro group, $R^1$ is a hydrogen atom, methyl, ethyl, butyl or propyl group, $R^2$ is a hydrogen atom, methyl, c-propylmethyl, trifluoroethyl, N,N-diethylaminoethyl, or methylsulfonylethyl group, and $R^3$ is a trifluoromethyl, phenyl, fluorophenyl or chlorophenyl group.

* * * * *